United States Patent [19]
Watanabe et al.

[11] Patent Number: 5,827,920
[45] Date of Patent: Oct. 27, 1998

[54] EMULSION COMPOSITION

[75] Inventors: Kei Watanabe; Hiroyuki Kakoki; Kenzo Ito, all of Yokohama, Japan

[73] Assignee: Shiseido Company, Ltd., Tokyo, Japan

[21] Appl. No.: 793,443

[22] PCT Filed: Jun. 28, 1996

[86] PCT No.: PCT/JP96/01803

§ 371 Date: May 12, 1997

§ 102(e) Date: May 12, 1997

[87] PCT Pub. No.: WO97/02090

PCT Pub. Date: Jan. 23, 1997

[30] Foreign Application Priority Data

Jun. 30, 1995 [JP] Japan ..................................... 7-166474

[51] Int. Cl.$^6$ .............................. C08L 31/02; C08L 83/04
[52] U.S. Cl. ........................... 524/833; 424/59; 424/70.9; 424/70.12; 424/78.03; 524/837
[58] Field of Search ..................... 524/833, 837; 424/59, 70.9, 70.12, 78.03, 401

[56] References Cited

U.S. PATENT DOCUMENTS

| | | | |
|---|---|---|---|
| 5,306,485 | 4/1994 | Robinson et al. | 424/59 |
| 5,322,689 | 6/1994 | Hughes et al. | 424/401 |
| 5,567,426 | 10/1996 | Nadaud et al. | 424/401 |
| 5,585,104 | 12/1996 | Ha et al. | 424/401 |
| 5,641,493 | 6/1997 | Date et al. | 424/401 |

FOREIGN PATENT DOCUMENTS

| | | |
|---|---|---|
| 5-97644 | 4/1993 | Japan . |
| 7-149621 | 6/1995 | Japan . |
| 7-206629 | 8/1995 | Japan . |

*Primary Examiner*—Margaret W. Glass
*Attorney, Agent, or Firm*—Foley & Lardner

[57] ABSTRACT

An emulsion compositions comprising (i) an alkyl-modified carboxyvinyl polymer, (ii) a $C_{12}$ to $C_{18}$ higher alcohol solid at room temperature (for example 15° to 20° C.), and (iii) a silicone oil, wherein the weight ratio of the component (i)/component (ii) is not more than 0.5. This emulsion further contains no surfactant.

17 Claims, No Drawings

EMULSION COMPOSITION

TECHNICAL FIELD

The present invention relates to an emulsion composition. More specifically, it relates to an emulsion compositions having little stickiness to the skin, a superior rich feeling of use, and a good emulsion stability.

BACKGROUND ART

As the emulsion compositions for cosmetics creams, emulsions, etc. using various types of oil-based and water-based components and surfactants have been widely used in the past. In recent years, however, greater safety has been desired in cosmetics as well. From this viewpoint, the presence of surfactants has been considered a problem. Therefore, it may be considered to formulate an emulsion composition for a cosmetic without using a surfactant. As such a method, there is the method of formulating the emulsion composition for the cosmetic using an alkyl-modified carboxyvinyl polymer, but this emulsion composition is deficient in that it does not have a sufficiently good feeling of use, in particular, lacks rich feeling when applied to the skin, and suffers from stickiness and sliminess after drying.

DISCLOSURE OF INVENTION

Accordingly, the object of the present invention is to provide an emulsion composition, even without using a surfactant, having little stickiness or sliminess, a good rich feeling of use, and a good emulsion stability.

In accordance with the present invention, there is provided an emulsion composition comprising (i) an alkyl-modified carboxyvinyl polymer, (ii) a $C_{12}$ to $C_{28}$ higher alcohol which is solid at room temperature and (iii) a silicone oil, wherein the weight ratio of the component (i)/component (ii) is not more than 0.5.

BEST MODE FOR CARRYING OUT THE INVENTION

The present inventors engaged in intensive research to solve the above-mentioned problem and, as a result, found that, by incorporating, into the emulsion composition, an alkyl-modified carboxyvinyl polymer, a solid higher alcohol, and a silicone oil, wherein the weight ratio of the component (i)/component (ii) is made 0.5 or less, it is possible to obtain a good rich feeling of use having little stickiness or sliminess, and a high emulsion stability, whereby the present invention has been completed.

The emulsion composition of the present invention is characterized in that it substantially does not contain any surfactant. Further, the content of the solid higher alcohol is preferably 0.01 to 10% by weight and the content of the silicone oil is preferably 1 to 30% by weight.

The constitution of the emulsion composition of the present invention will now be explained.

The alkyl-modified carboxyvinyl polymer (powder) usable as the component (i) in the emulsion composition of the present invention may include an acrylic acid-methacrylic acid alkyl copolymer, for example, those commercially available under the brand names of CARBOPOL 1342, PEMULEN TR-1, and PEMULEN TR-2 (BF Goodrich Company). These alkyl-modified carboxyvinyl polymers may be used alone or in any mixtures of two or more types. Further, the formulation amount is preferably 0.01 to 10% by weight based upon the total weight of the emulsion composition. Further, from the viewpoint of the feeling of use, a range of 0.05 to 5% by weight based upon the total weight of the emulsion composition is more preferable. If the formulation amount is less than 0.01% by weight, the emulsification is difficult, whereas the amount 10% by weight, no further increase in the emulsification action and effect of improvement of the emulsion stability can be expected. Note that with a non-alkyl-modified carboxyvinyl polymer (for example, CARBOPOL 941 (BF Goodrich Co.), Hybis Wako-105 (Wako Pure Chemicals) etc. ordinarily used as a thickener, it is not possible to stably emulsify the oil component.

The $C_{12}$ to $C_{28}$ (preferably $C_6$ to $C_{22}$) higher alcohol usable as the component (ii) in the emulsion composition of the present invention and solid at room temperature (for example, 15° to 20° C.) may be used alone or in any mixture thereof. As specific examples, straight chain alcohols such as lauryl alcohol, cetyl alcohol, stearyl alcohol, behenyl alcohol, myristyl alcohol, cetostearyl alcohol, and branched chain alcohols such as glyceryl monostearyl ethers (batyl alcohol), glyceryl monocetyl ethers (chimyl alcohol), may be mentioned.

If the higher alcohol used as the component (ii) in the present invention has less than 12 carbon atoms, it becomes liquid at room temperature and the effect of the present invention cannot be obtained, whereas if it has 29 carbon atoms or more, the melting point becomes high and emulsification becomes difficult.

As the formation amount of the higher alcohol, 0.01 to 10% by weight based upon the total weight of the emulsion composition, preferably 0.05 to 5% by weight, is used. If the formulation amount is less than 0.01% by weight, the effect (imparting of the rich feeling) is not exhibited much at all, whereas even if more than 10% by weight, not much further improvement in the desired effect is recognized.

The ratio of the components (i) and (ii) mixed in the emulsion composition according to the present invention must be not more than 0.5, preferably 0.03 to 0.4. If this ratio is more than 0.5 (if the alkyl-modified carboxyvinyl polymer becomes too much), the slimy feeling distinctive to a polymer is felt, and therefore, this is not preferable from the viewpoint of the usability.

As the silicone oil usable as the component (iii) in the emulsion composition of the present invention, chain type silicones, such as dimethyl polysiloxane, methylphenylpolysiloxane, methylhydrogenpolysiloxane, and cyclic type silicones such as octamethylcyclotetrasiloxane, decamethylcyclopentasiloxane, dodecamethylcyclohexasiloxane may be used. As the amount of the silicone oil added, 1 to 30% by weight of the total weight of the emulsion composition is preferred and is more preferably is 5 to 20% by weight. If the formulation amount is less than 1% by weight, the effect (reduction of stickiness) is not exhibited much at all, while conversely even if more than 30% by weight, not much improvement is observed in the desired effect.

The emulsion composition of the present invention may include, in addition to the above-mentioned essential components, various types of ingredients conventionally used for cosmetics to an extent not impairing the object of the present invention. In particular, solid oils and fats and/or semisolid oils and fats other than the higher alcohols which are solid at room temperature are preferably formulated therein in an amount less than 2% by weight based upon the total weight of the emulsion composition. This is because, if the formulation amount is more than 2% by weight, stickiness is liable to be felt—which is not preferred in terms of the usability.

As the liquid oils and fats, there are linseed oil, tsubaki oil, macadamia nut oil, corn oil, mink oil, olive oil, avocado oil, sasanqua oil, castor oil, safflower oil, apricot oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, teaseed oil, evening primrose oil, eggyoke oil, neetsfoot oil, liver oil, triglycerine, glycerine trioctanate, pentaerythritol tetraoctanate, glycerine triisopalmitate, etc.

As the solid oils and fats, there are cacao fat, coconut oil, palm oil, palm nut oil, beef tallow, hog fat, sheep fat, horse fat, hydrogenated oil, hydrogenated castor oil, Japan wax, Shea Butter, etc.

As waxes, there are beeswax, candelilla wax, cotton wax, carnauba wax, bayberry wax, tree wax, spermaceti, montan wax, rice bran wax, lanolin, reduced lanolin, hard lanolin, kapok wax, sugarcane wax, jojoba wax, shellac wax, etc.

As ester oils, there are octanic acid esters such as cetyl octanate, lauric acid esters such as hexyl laurate, myristate acid esters such as isopropyl myuristate, octyldodecyl myristate, palmitic acid esters such as octyl palmitate, stearic acid esters such as isocetyl stearate, isostearic acid esters such as isopropyl isostearate, isopalmitic acid esters such as octyl isopalmitate, oleic acid esters such as isodecyl oleate, adipic acid diesters such as diisopropyl adipate, sebacic acid diesters such as diethyl sebacate, diisostearyl malate, glyceryl tri-2-ethylhexanoate, pentaerythritol tetra-2-ethylhexanoate, 2-ethylhexyl succinate, etc.

As hydrocarbon oils, there are liquid paraffin, ozocerite, squalane, squalene, pristane, paraffin, isoparaffin, ceresin, vaseline, microcrystalline wax, etc.

As lower alcohols, there are methanol, ethanol, propanol, isopropanol, etc.

As sterols, there are cholesterols, cytosterols, phytosterols, lanosterols, etc.

As humectants, there are polyethylene glycol, propylene glycol, dipropylene glycol, 1,3-butylene glycol, hexylene glycol, glycerine, diglycerine, xylitol, maltitol, maltose, erythritol, trepharose, D-mannitol, gluten, glucose, fructose, lactose, sodium chondroitin sulfate, sodium hyalonate, sodium adenosine phosphate, sodium lactate, gallates, pyrrolidone carbonates, glucosamine, cyclodextrin, etc.

As water-soluble polymers, there are plant or vegetable-based polymers such as arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, animal-based polymers such as collagen, casein, albumin, gelatin, starch-based polymers such as carboxymethyl starch, methylhydroxypropyl starch, cellulose-based polymers such as methyl cellulose, nitrocellulose, ethyl cellulose, methylhydroxypropyl cellulose, hydroxyethyl cellulose, sodium cellulose sulfate, hydroxypropyl cellulose, sodium carboxymethyl cellulose, crystalline cellulose, cellulose powder, alginic acid-based polymers such as sodium alginate, alginic acid propylene glycol esters, vinyl polymers such as polyvinylmethyl ethers, carboxyvinyl polymers (CARBOPOL etc.), polyoxyethylene polymers, polyoxyethylene-polyoxypropylene copolymer polymers, acrylate polymers such as sodium polyacrylate, polyethylacrylate, polyacrylamide, polyethyleneimine, cation polymers, inorganic water-soluble polymers such as bentonite, aluminum magnesium silicate, laponite, hectonite, anhydrous silicic acid, etc.

As UV absorbants, there are benzoic acid-based UV absorbants such as para-aminobenzoic acid, anthranilic acid-based UV absorbants such as methyl anthranilate, salicylic acid based UV absorbants such as octyl salicylate, phenyl salicylate, homomethyl salicylate, cinnamic acid based UV absorbants such as isopropyl paramethoxycinnamate, octylparamethoxycinnamate, 2-ethylhexyl paramethoxycinnamate, glyceryl diparamethoxycinnamate mono-2-ethylhexanate, [4-bis(trimethylsiloxy) methylsilyl-3-methylbutyl]-3,4,5-trimethoxycinnamic acid esters, benzophenone based UV absorbants such as 2,4-dihydroxybenzophenone, 2-hydroxy-4-methoxybenzophenone, 2-hydroxy-4-methoxybenzophenone-5-sulfonic acid, sodium 2-hydroxy-4-methoxybenzophenone-5-sulfonic acid, urocanic acid, ethyl urocanate, 2-phenyl-5-methylbenzoxazole, 2-(2'-hydroxy-5'-methylphenyl) benzotriazole, 4-tert-butyl-4'-methoxybenzoylmethane, etc.

As chelating agent, there are alanine, sodium edetate, sodium polyphosphate, sodium metaphosphate, phosphoric acid, etc.

As neutralizing agents, there are 2-amino-2-methyl-1-propanol, 2-amino-2-methyl-1,3-propanediol, potassium hydroxide, sodium hydroxide, triethanolamine, sodium carbonate, etc.

As pH adjusters, there are lactic acid, citric acid, glycolic acid, succinic acid, tartaric acid, dl-malic acid, potassium carbonate, sodium hydrogencarbonate, ammonium hydrogencarbonate, etc.

As antioxidants, there are ascorbic acid, α-tocopherol, dibutylhydroxytoluene, butylhydroxyanisole, etc.

As antibacterials, there are benzoic acid, salicylic acid, carbolic acid, sorbic acid, paraoxybenzoic acid esters, parachlorometacresol, hexachlorophene, benzalkonium chloride, chlorohexidine chloride, trichlorocarbanilide, Photosensitizer phenoxyethanol, etc.

As medicines, there are vitamins such as vitamin A oil, retinol, retinol palmitate, inositol, pyridoxine chlorate, benzyl nicotinate, nicotinic acid amide, dl-α-tocopherol nicotinate, magnesium ascorbate phosphate, vitamin $D_2$ (ergocalciferol), dl-α-tocopherol, dl-α-tocopherol acetate, pantothenic acid, biotin, hormones such as estradiol, ethynylestradiol, antipyretics such as alginin, asparagic acid, cystine, cysteine, methionine, serine, leucine, tryptophan, and other amino acids, allantoin, glycyrrhetinic acid, tranexamic acid, azulene, whiteners such as arbutin, astringents such as zinc oxide, tannic acid, fresheners such as L-menthol, camphor, and sulfur, lysozyme chloride, pyridoxine chlorate, γ-orizanol, etc.

As various types of extracts, there are Houttuynia cordate extract, Phellodendron Bark extract, melilot extract, white dead nettle extract, licorice root extract, herbaceous peony extract, soapwort extract, dishcloth gourd extract, cinchona extract, creeping saxifrage extract, Sophora angustifolia extract, candock extract, common fennel extract, primrose extract, rose extract, Rehmannia glutinosa extract, lemon extract, shikon extract, alloe extract, iris bulb extract, eucalyptus extract, field horsetail extract, sage extract, thyme extract, tea extract, laver extract, cucumber extract, clove extract, raspberry extract, melissa extract, Ginseng extract, carrot extract, horse chestnut extract, peach extract, peach leaf extract, mulberry extract, cornflower extract, hamamelis extract, placenta extract, thymus extract, silk extract, etc.

Further, the above-mentioned medicines may not only be used in a free state, but also be used in the form of a salt of an acid or base in the case capable of forming a salt or in the form of an ester in the case of having a carboxylic acid group.

In addition to the above, it is also possible to formulate therein a silicone resin, silicone rubber, etc.

Further, the emulsion composition of the present invention may include therein, if necessary, a suitable fragrance, color, etc. to an extent not impairing the emulsion stability.

Further, if a surfactant such as a monoglyceride, sorbitan fatty acid ester, polyglycerine fatty acid ester, polyoxyethylene hardened castor oil, polyoxyethylene fatty acid ether, is added thereto in a small amount, the stability is further improved.

Further, as the method for preparing the emulsion composition of the present invention, emulsifiers usually used for emulsification such as a homomixer, homodisper, may be used, but if it is prepared by an emulsifier having a high shearing force such as an ultrasonic wave emulsifier, high pressure emulsifier, the usability and stability are further improved.

EXAMPLES

The present invention will now be explained in further detail by, but is of course not limited to, the Examples. Note that the formulation amounts shown below are all % by weight.

The emulsion composition of the present invention was evaluated based upon the evaluation methods shown below:

1) Organoleptic test by panel of female experts

The feeling of use as an emulsion composition was evaluated by performing an organoleptic test with a panel of 25 women using the following evaluation criteria.

(Evaluation criteria of richness)

o: Good (at least 20 out of 25 evaluated emulsion as good)

Δ: Somewhat good (10 to 19 out of 25 evaluated emulsion as good)

x: Poor (9 or less out of 25 evaluated emulsion as good)

Note that "richness" means a full, rich feeling at the time of use.

(Evaluation criteria of stickiness)

o: Good (at least 20 out of 25 evaluated emulsion as good)

Δ: Somewhat good (10 to 19 out of 25 evaluated emulsion as good)

x: Poor (9 or less out of 25 evaluated emulsion as good)

(Evaluation criteria of sliminess)

o: Good (at least 20 out of 25 evaluated emulsion as good)

Δ: Somewhat good (10 to 19 out of 25 evaluated emulsion as good)

x: Poor (9 or less out of 25 evaluated emulsion as good)

2) Stability test

The state of the emulsion composition after being allowed to stand in a 50° C. thermostatic vessel for one month was observed and the stability evaluated by the following evaluation criteria:

(Evaluation criteria of stability)

o: No separation of oil observed at all

Δ: Slight separation of oil observed x: Clear separation of oil observed

Examples 1 to 3 and Comparative Example 1 to 4

The emulsions having the compositions shown in Table 1 were prepared by first heating the oil phase components to liquify them, then emulsifying them by an emulsifier while adding the aqueous phase components. The resultant emulsion compositions were then evaluated by the above-mentioned criteria. The results are also shown in Table 1.

TABLE 1

| Component | Ex. 1 | Ex. 2 | Ex. 3 | Comp. Ex. 1 | Comp. Ex. 2 | Comp. Ex. 3 | Comp. Ex. 4 |
| --- | --- | --- | --- | --- | --- | --- | --- |
| A. Oil phase | | | | | | | |
| Liquid paraffin | 22.0 | 22.0 | 30.0 | 22.0 | 22.0 | 22.0 | 22.0 |
| Stearyl aldohol | 3.0 | 5.0 | 3.0 | 3.0 | 3.0 | — | — |
| Dimethylpolysiloxane | 5.0 | 5.0 | 5.0 | 5.0 | — | 5.0 | — |
| B. Aqueous phase | | | | | | | |
| PEMULEN TR-1 | 0.2 | 0.2 | 0.2 | — | 0.2 | 0.2 | 0.2 |
| CARBOPOL 941 | — | — | — | 0.2 | — | — | — |
| Triethahol amine | 0.4 | 0.4 | 0.4 | 0.4 | 0.4 | 0.4 | 0.4 |
| Propylene glycol | 10.0 | 10.0 | 10.0 | 10.0 | 10.0 | 10.0 | 10.0 |
| Ethyl alcohol | 5.0 | 5.0 | 5.0 | 5.0 | 5.0 | 5.0 | 5.0 |
| Methyl paraoxybenzoate | 0.1 | 0.1 | 0.1 | 0.1 | 0.1 | 0.1 | 0.1 |
| Trisodium edetate | 0.1 | 0.1 | 0.1 | 0.1 | 0.1 | 0.1 | 0.1 |
| Ion exchanged water | Balance | Balance | Balance | Balance | Balance | Balance | Balance |
| PEMULEN/higher alcohol | 0.06 | 0.04 | 0.06 | — | 0.06 | — | — |
| Emulsion stability | o | o | o | x | o | o | o |
| Richness | o | o | o | o | o | x | Δ |
| Stickiness | o | o | o | o | x | o | x |
| Sliminess | o | o | o | o | o | x | x |

As shown in Table 1, it is clear that the emulsion compositions of Examples 1 to 3 were superior in terms of the richness, excellent feeling of use having little stickiness, and good emulsion stability.

Example 4

The same procedure was followed as in Example 1 to prepare an emulsion having the composition shown below and to evaluate the usability thereof, whereupon it is clear that the emulsion composition of this Example, like Example 1, is a superior in terms of richness, a feeling of use having little stickiness, and a good emulsion stability.

| A. | Oil phase | |
|---|---|---|
| | Dimethyl Polysiloxane | 10.0% |
| | Isopropyl myristate | 8.0 |
| | Squalane | 2.0 |
| | α-Tocopherol | 0.3 |
| | Cetyl alcohol | 3.0 |
| B. | Aqueous phase | |
| | Triethanolamine | 0.25% |
| | Propylene glycol | 10.0 |
| | Methyl paraoxybenzoate | 0.1 |
| | Sodium metaphosphate | 0.1 |
| | CARBOPOL 1342 | 0.3 |
| | Hydroxypropylmethylcellulose | 0.1 |
| | Ion exchanged water | Balance |

Example 5

| A. | Oil phase | |
|---|---|---|
| | Liquid paraffin | 10.0% |
| | Dimethyl polysiloxane | 1.0 |
| | Jojoba oil | 4.0 |
| | Vitamin A oil | 0.1 |
| | Batyl alcohol | 5.0 |
| B. | Aqueous phase | |
| | 1,3-butylene glycol | 10.0% |
| | Propylene glycol | 3.0 |
| | Arbutin | 2.0 |
| | Magnesium ascorbate phosphate | 1.0 |
| | Placenta extract | 0.5 |
| | Dishcloth gourd extract | 2.0 |
| | PEMULEN TR-1 | 0.02 |
| | CARBOPOL 941 | 0.15 |
| | Trisodium edetate | 0.15 |
| | Methyl paraoxybenzoate | 0.1 |
| | Phenoxy ethanol | 0.2 |
| | Ion exchanged water | Balance |

Examples 6 to 7 and Comparative Examples 5 to 6

TABLE 2

| | Ex. 6 | Comp. Ex. 5 | Ex. 7 | Comp. Ex. 6 |
|---|---|---|---|---|
| A. Oil phase | | | | |
| Liquid paraffin | 22.0 | 22.0 | 22.0 | 22.0 |
| Stearyl alcohol | 1.0 | 0.2 | 1.0 | 0.2 |
| Dimethylpolysiloxane | 5.0 | 5.0 | 5.0 | 5.0 |
| Vaseline | 1.0 | 1.0 | 4.0 | 4.0 |
| B. Aqueous phase | | | | |
| PEMULEN TR-2 | 0.2 | 0.2 | 0.2 | 0.2 |
| Triethanolamine | 0.4 | 0.4 | 0.4 | 0.4 |
| 1,3-butylene glycol | 10.0 | 10.0 | 10.0 | 10.0 |
| Ethyl alcohol | 5.0 | 5.0 | 5.0 | 5.0 |
| Methyl paraoxy-benzoate | 0.1 | 0.1 | 0.1 | 0.1 |
| Trisodium edetate | 0.1 | 0.1 | 0.1 | 0.1 |
| Ion exchanged water | Balance | Balance | Balance | Balance |
| PEMULEN TR-2/higher alcohol | 0.2 | 1.0 | 0.2 | 1.0 |
| other solid oils and fats | 1.0 | 1.0 | 4.0 | 4.0 |
| Sliminess | ○ | x | ○ | x |
| Stickiness | ○ | ○ | Δ | x |
| Richness | ○ | ○ | ○ | ○ |
| Emulsion stability | ○ | ○ | ○ | ○ |

As shown in Table 2, Example 6, where the weight ratio of the alkyl-modified carboxyvinyl polymer and higher alcohol and the amounts formulated of the solid oils and fats and/or semisolid oils and fats other than the higher alcohol are in a suitable range, gives an emulsion excellent in terms of both sliminess and stickiness. The emulsion composition of Example 7 also poses no practical problems.

Example 8

The same procedure was followed as in Example 1 to prepare an emulsion having the composition shown below and to evaluate its usability, whereupon it is clear that the emulsion composition of this Example is a superior in terms of richness, a feeling of use having little stickiness or sliminess, and a good emulsion stability.

| A. | Oil phase | |
|---|---|---|
| | Dimethyl polysiloxane | 8.0% |
| | Isopropyl myristate | 2.0 |
| | Squalane | 2.0 |
| | Cetostearyl alcohol | 1.0 |
| | Vaseline | 1.0 |
| B. | Aqueous phase | |
| | Triethanolamine | 0.4% |
| | Glycerol | 8.0 |
| | Methyl paraoxybenzoate | 0.1 |
| | CARBOPOL 1342 | 0.2 |
| | Xanthane gum | 0.1 |
| | Ion exchanged water | Balance |

Example 9

A high pressure emulsifier was used to prepare an emulsion having the composition shown below, then this was evaluated for its usability. It is clear that the emulsion composition of this Example was rich and a feeling of use having little stickiness or sliminess and further a superior emulsion stability.

| A. | Oil phase | |
|---|---|---|
| | Decamethylcyclopentasiloxane | 8.0% |
| | Macadamia nut oil | 3.0 |
| | Squalane | 2.0 |
| | Behenyl alcohol | 0.4 |
| | Batyl alcohol | 0.2 |
| | Solid paraffin | 0.5 |
| | Vaseline | 1.2 |
| B. | Aqueous phase | |
| | Triethanolamine | 0.4% |
| | Glycerol | 8.0 |
| | Methyl paraoxybenzoate | 0.1 |
| | PEMULEN TR-1 | 0.2 |
| | Xanthane gum | 0.1 |
| | Ion exchanged water | Balance |

INDUSTRIAL APPLICABILITY

As explained above, according to the present invention, it is possible to obtain a superior emulsion composition, without using a surfactant, having a rich feeling, a superior feeling of use with, for example, lack of stickiness, and a good emulsion stability.

We claim:

1. An emulsion composition comprising (i) an acrylic acid-methacrylic acid alkyl copolymer, (ii) a $C_{12}$ to $C_{28}$ higher alcohol which is solid at room temperature, and (iii) a silicone oil, the weight ratio of the component (i)/component (ii) being not more than 0.5, with the proviso that said composition includes no surfactant.

2. An emulsion composition as claimed in claim 1, wherein the content of the higher alcohol which is solid at room temperature is 0.01 to 10% by weight based on the total weight of the emulsion composition.

3. An emulsion composition as claimed in claim 2, wherein the content of the silicone oil is 1 to 30% by weight based on the total weight of the emulsion composition.

4. An emulsion composition as claimed in claim 2, further comprising solid oil in addition to the higher alcohol which is solid at room temperature, in an amount of more than 0% but less than 2% by weight based upon the total weight of the emulsion composition.

5. An emulsion composition as claimed in claim 1, wherein the content of the silicone oil is 1 to 30% by weight based on the total weight of the emulsion composition.

6. An emulsion composition as claimed in claim 5, further comprising solid oil in addition to the higher alcohol which is solid at room temperature, in an amount of more than 0% but less than 2% by weight based upon the total weight of the emulsion composition.

7. An emulsion composition as claimed in claim 1, further comprising solid oil in addition to the higher alcohol which is solid at room temperature, in an amount of more than 0% but less than 2% by weight based upon the total weight of the emulsion composition.

8. An emulsion composition as claimed in claim 7, wherein said further solid oil is selected from the group consisting of cacao fat, coconut oil, palm oil, palm nut oil, beef tallow, hog fat, sheep fat, horse fat, hydrogenated oil, hydrogenated castor oil, Japan wax, and Shea butter.

9. An emulsion composition as claimed in claim 1, wherein said $C_{12}$ to $C_{28}$ higher alcohol is selected from the group consisting of lauryl alcohol, cetyl alcohol, stearyl alcohol, behenyl alcohol, myristyl alcohol, cetostearyl alcohol, glyceryl monostearyl ethers, and glyceryl monocetyl ethers.

10. An emulsion composition as claimed in claim 1, wherein said silicone oil is selected from the group consisting of dimethyl polysiloxane, methylphenylpolysiloxane, methylhydrogenpolysiloxane, octamethylcyclotetrasiloxane, decamethylcyclopentasiloxane, and dodecamethylcyclohexasiloxane.

11. An emulsion composition as claimed in claim 1, further comprising at least one component selected from the group consisting of a liquid oil, a solid oil, a wax, an ester oil, a hydrocarbon oil, a lower alcohol, a sterol, a humectant, a water soluble polymer, a UV absorbant, a chelating agent, a neutralizing agent, a pH adjuster, an antioxidant, an antibacterial, a medicine, an extract, a resin, a fragrance, and a color.

12. A method for preparing an emulsion according to claim 1, comprising combining acrylic acid-methacrylic acid alkyl copolymer, said $C_{12}$ to $C_{28}$ higher alcohol which is solid at room temperature, and said silicone oil, optionally by using a homomixer or by using an emulsifier.

13. A method for preparing a cosmetic comprising employing a composition as claimed in claim 1.

14. An emulsion composition comprising (i) an acrylic acid-methacrylic acid alkyl copolymer, (ii) a $C_{12}$ to $C_{28}$ higher alcohol which is solid at 15° C. to 20° C., and (iii) a silicone oil, the weight ratio of the component (i)/component (ii) being not more than 0.5, with the proviso that the composition includes no surfactant.

15. An emulsion composition as claimed in claim 14, wherein the content of the higher alcohol which is solid at room temperature is 0.01 to 10% by weight, based on the total weight of the emulsion composition.

16. An emulsion composition as claimed in claim 14, wherein the content of the silicone oil is 1 to 30% by weight based on the total weight of the emulsion composition.

17. An emulsion composition as claimed in claim 14, further comprising solid oil in addition to the higher alcohol which is solid at 15° C. to 20° C. in an amount of more than 0% but less than 2% by weight based upon the total weight of the emulsion composition.

* * * * *